(12) United States Patent
Takeuchi et al.

(10) Patent No.: US 7,833,153 B2
(45) Date of Patent: Nov. 16, 2010

(54) ENDOSCOPE

(75) Inventors: Yasuo Takeuchi, Hachioji (JP); Toru Shinmura, Hachioji (JP); Kaoru Tsuruoka, Kawasaki (JP)

(73) Assignee: Olympus Medical Systems Corporation (JP)

(*) Notice: Subject to any disclaimer, the term of this patent is extended or adjusted under 35 U.S.C. 154(b) by 924 days.

(21) Appl. No.: 11/682,548

(22) Filed: Mar. 6, 2007

(65) Prior Publication Data
US 2007/0212913 A1   Sep. 13, 2007

(30) Foreign Application Priority Data
Mar. 7, 2006   (JP) .............................. 2006-061519

(51) Int. Cl.
*A61B 1/00* (2006.01)
(52) U.S. Cl. ...................................... 600/137; 600/144
(58) Field of Classification Search ................ 600/136, 600/137, 139, 141, 142, 144, 148
See application file for complete search history.

(56) References Cited

U.S. PATENT DOCUMENTS

| | | | | |
|---|---|---|---|---|
| 4,911,148 A | * | 3/1990 | Sosnowski et al. | 600/136 |
| 4,977,887 A | * | 12/1990 | Gouda | 600/144 |
| 5,275,614 A | | 1/1994 | Haber et al. | |
| 5,810,715 A | * | 9/1998 | Moriyama | 600/144 |
| 5,885,207 A | * | 3/1999 | Iwasaka | 600/139 |
| 5,976,074 A | * | 11/1999 | Moriyama | 600/144 |
| 6,203,494 B1 | * | 3/2001 | Moriyama | 600/144 |
| 6,749,572 B2 | | 6/2004 | Edwardsen et al. | |
| 2002/0133077 A1 | | 9/2002 | Edwardsen et al. | |

FOREIGN PATENT DOCUMENTS

| | | |
|---|---|---|
| JP | 7-345 | 1/1995 |
| JP | 2004-305413 | 11/2004 |

OTHER PUBLICATIONS

Search Report dated Nov. 20, 2007 issued in counterpart European Application No. 07004020.9-1265.

* cited by examiner

*Primary Examiner*—Linda C Dvorak
*Assistant Examiner*—Alireza Nia
(74) *Attorney, Agent, or Firm*—Ostrolenk Faber LLP (57) ABSTRACT

An endoscope includes an operation portion side member, an insertion portion side member rotatable integrally with the insertion portion, an elastic member provided in one of the operation portion side member and the insertion portion side member, a frictional surface which is provided in the other of the operation portion side member and the insertion portion side member and which generates a frictional force between the frictional surface and the elastic member when the frictional surface is pressed onto the elastic member and the insertion portion is rotated, and a movement adjusting mechanism which relatively moves the operation portion side member and the insertion portion side member to continuously adjust press force acting between the elastic member and the frictional surface while deforming the elastic member.

6 Claims, 6 Drawing Sheets

ENDOSCOPE

CROSS-REFERENCE TO RELATED APPLICATIONS

This application is based upon and claims the benefit of priority from prior Japanese Patent Application No. 2006-061519, filed Mar. 7, 2006, the entire contents of which are incorporated herein by reference.

BACKGROUND OF THE INVENTION

1. Field of the Invention

The present invention relates to an endoscope whose insertion portion is rotatable in a direction around a central axis thereof with respect to an operation portion.

2. Description of the Related Art

In an insertion portion of an endoscope, a bending portion is used which is operated to bend in four vertical and horizontal directions, but a bending portion is also used which is operated to only bend in two directions in order to simplify a bending mechanism for a smaller diameter of the insertion portion. In such a two-way bending endoscope, the insertion portion is rotated halfway in a direction around a central axis thereof to achieve vertical and horizontal bending.

In an endoscope in Jpn. Pat. Appln. KOKAI Publication No. 7-345, an insertion portion can be switched among the following states: a state where the insertion portion is rotatable with respect to an operation portion; a state where the insertion portion is provided with predetermined force urging to rotate with respect to the operation portion; and a state where the insertion portion is fixed with respect to the operation portion. In the state where the insertion portion is provided with the predetermined force urging to rotate, the insertion portion can be rotated by providing a force equal to or greater than the force urging to rotate and the insertion portion can be automatically returned to an original state by releasing this force.

In an endoscope in Jpn. Pat. Appln. KOKAI Publication No. 2004-305413, an insertion portion connecter at a proximal end of an insertion portion is internally fitted into an operation portion connecter at a distal end of an operation portion rotatably in a direction around an axis thereof. On an inner peripheral surface of the operation portion connecter and an outer peripheral surface of the insertion portion connecter, there are formed tapered surfaces which are pressed slidably on each other and which increase in diameter toward a distal side. Between these tapered surfaces, there is interposed an O-ring as a frictional force generating member, so that the insertion portion is not rotated with respect to the operation portion by a force equal to or less than the given force.

In an endoscope in the specification of U.S. Pat. No. 6,749,572, a rotation control wheel externally fitted onto and fixed to a proximal end of an insertion portion can be rotationally operated to rotate the insertion portion. Then, a brake handle disposed at a distal end of an operation portion is rotationally driven to linearly drive a brake member so that the brake member is pressed on the rotation control wheel, and thus the rotation control wheel is fixed to the brake member, thereby making it possible to fix the insertion portion to the operation portion.

BRIEF SUMMARY OF THE INVENTION

In an aspect of the present invention, an endoscope comprises: an operation portion; an elongate insertion portion whose one end is connected to the operation portion rotatably in a direction around a central axis of the insertion portion with respect to the operation portion; an operation portion side member provided in the operation portion; an insertion portion side member provided in the insertion portion and rotatable integrally with the insertion portion; an elastic member provided in one of the operation portion side member and the insertion portion side member; a frictional surface which is provided in the other of the operation portion side member and the insertion portion side member and which generates a rotation resisting frictional force between the frictional surface and the elastic member when the frictional surface is pressed onto the elastic member and the insertion portion is rotated; and a movement adjusting mechanism which relatively moves the operation portion side member and the insertion portion side member to continuously adjust the press force acting between the elastic member and the frictional surface while deforming the elastic member.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

A first embodiment of the present invention will hereinafter be described with reference to FIG. 1 to FIG. 4.

Figure 1:
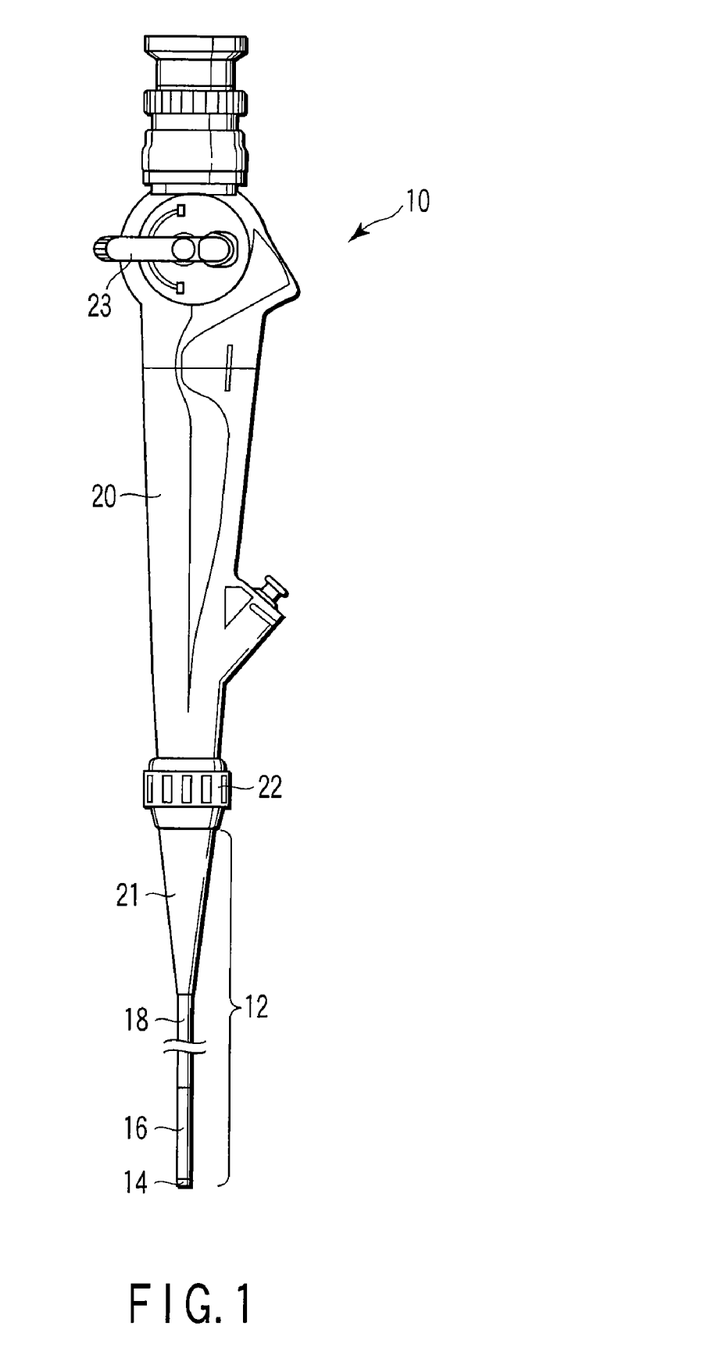
FIG. 1 is a side view showing an endoscope in a first embodiment of the present invention.

Referring to FIG. 1, an endoscope 10 in the present embodiment has an elongate insertion portion 12 to be inserted in a body cavity. This insertion portion 12 is formed by a distal rigid portion 14, a bending portion 16 operated to bend in two directions, and a long flexible tube portion 18, and these portions are linked in order from a distal side. A proximal end of the insertion portion 12 is connected to a distal end of an operation portion 20, and the insertion portion 12 is rotatable in a direction around a central axis thereof with respect to the operation portion 20. It is to be noted that the proximal end of the insertion portion 12 is provided with an anti-bending portion 21 for preventing the bending of the insertion portion 12 in the connection portion between the insertion portion 12 and the operation portion 20. Further, the distal end of the operation portion 20 is provided with an adjusting ring 22 for adjusting an operation force amount necessary for the rotational operation of the insertion portion 12 with respect to the operation portion 20. This adjusting ring 22 can be rotationally operated between a releasing position where the operation force amount is minimized and a fixing position where the operation force amount is maximized. Moreover, the proximal side of the operation portion 20 is provided with a bending lever 23 which is operated to bend the bending portion 16.

An operation force amount adjusting mechanism for adjusting the operation force amount will be described with reference to FIG. 2A to FIG. 4.

Figure 2A:
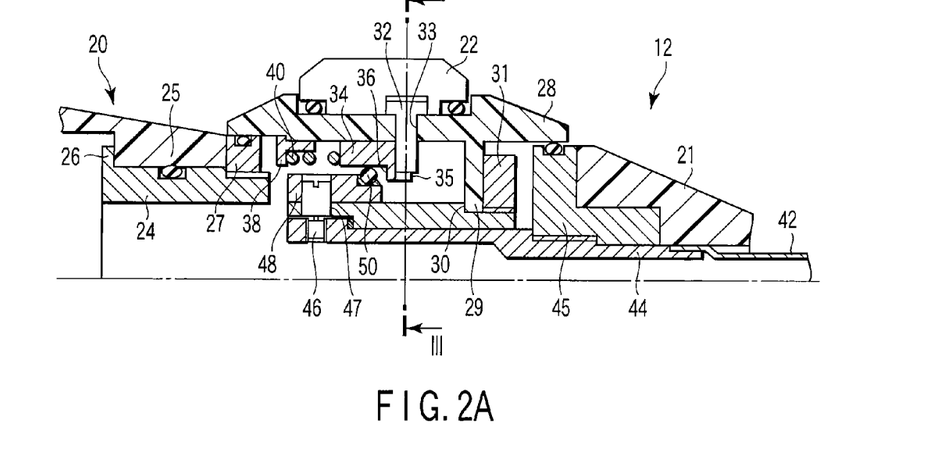
FIG. 2A is a longitudinal sectional view showing an operation force amount adjusting mechanism of the endoscope in a released state in the first embodiment of the present invention.

Referring to FIG. 2A, an operation portion connecter 24 protrudes from a distal end of a housing of the operation portion 20. That is, a distal side of the housing is substantially cylindrical, and a first fit convex portion 25 is provided to extend over the whole circumference on an inner peripheral surface at the distal end of the housing. A proximal side of the substantially cylindrical operation portion connecter 24 is inserted and fitted into a central opening of the first fit convex portion 25. A diametrically outwardly protruding second fit convex portion 26 is provided to extend over the whole circumference on an outer peripheral surface at a proximal end of the operation portion connecter 24. Further, a male screw is formed on an outer peripheral surface of an intermediate portion of the operation portion connecter 24, to which a first coupling ring 27 having a female screw formed on its inner peripheral surface is threaded. The first coupling ring 27 is screwed in so that the first fit convex portion 25 of the housing is held by the first coupling ring 27 and the second fit convex portion 26 at the proximal end of the operation portion connecter 24, thereby fixing the operation portion connecter 24 to the housing.

It is to be noted that an O-ring for maintaining watertightness is interposed between an inner peripheral surface of the first fit convex portion 25 of the housing and the outer peripheral surface of the operation portion connecter 24.

A connection ring 28 is externally fitted onto a distal side of the operation portion connecter 24 substantially coaxially. That is, a third fit convex portion 29 is provided to extend over the whole circumference on an inner peripheral surface on a distal side of the connection ring 28. The third fit convex portion 29 is fitted into a fit concave portion 30 provided to extend over the whole circumference on the outer peripheral surface on the distal side of the operation portion connecter 24. In the operation portion connecter 24, a male screw is formed adjacent to a distal side of the fit concave portion 30, and a second coupling ring 31 having a female screw formed in its inner peripheral surface is threaded to the male screw. The second coupling ring 31 is screwed in so that the third fit convex portion 29 of the connection ring 28 is held by the second coupling ring 31 and a proximal surface of the fit concave portion 30 of the operation portion connecter 24, thereby fixing the connection ring 28 to the operation portion connecter 24.

A proximal end of the connection ring 28 is externally fitted onto an outer peripheral surface of the first coupling ring 27 described above. Further, an O-ring for securing watertightness is interposed between the inner peripheral surface at the proximal end of the connection ring 28 and the outer peripheral surface of the first coupling ring 27.

Figure 3:
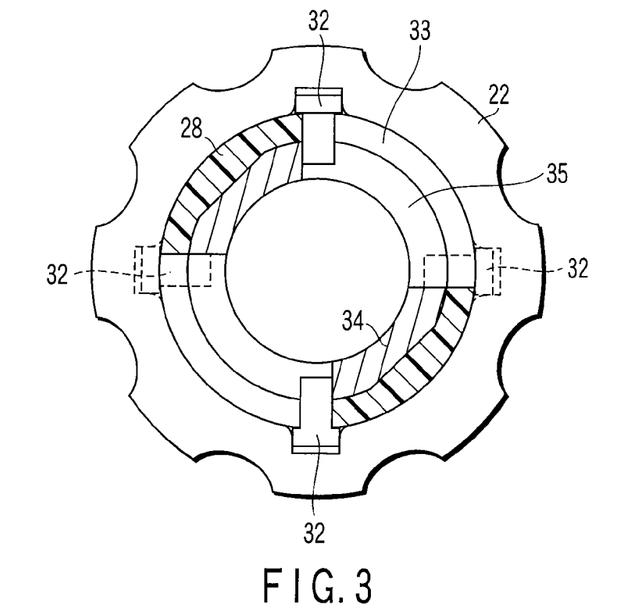
FIG. 3 is a transverse sectional view showing a cam mechanism of the operation force amount adjusting mechanism of the endoscope in the first embodiment of the present invention.
Figure 4:
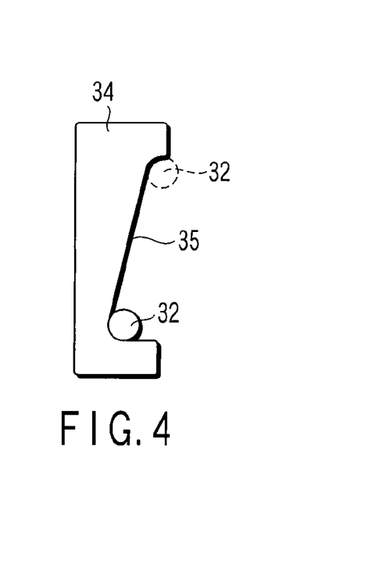
FIG. 4 is a schematic view showing the cam mechanism of the operation force amount adjusting mechanism of the endoscope in the first embodiment of the present invention.

Referring to FIG. 2A, FIG. 3 and FIG. 4, the adjusting ring 22 is externally fitted onto the connection ring 28 substantially coaxially, and this adjusting ring 22 is rotatable in a direction around a central axis thereof with respect to the connection ring 28. A cam pin 32 protrudes diametrically inwardly from an inner peripheral surface of an intermediate portion of the adjusting ring 22. This cam pin 32 is inserted slidably in a circumferential direction through a first penetrating groove 33 provided to extend substantially over 90° in the circumferential direction in the connection ring 28. Further, the cam pin 32 is in contact with a releasing side end wall of the first penetrating groove 33 when the adjusting ring 22 is at the releasing position (see full lines in FIG. 3), whereas the cam pin 32 is in contact with a fixing side end wall of the first penetrating groove 33 when the adjusting ring 22 is at the fixing position (see broken lines in FIG. 3).

It is to be noted that O-rings for securing watertightness are interposed on both sides of the cam pin 32 between an outer peripheral surface of the connection ring 28 and an inner peripheral surface of the adjusting ring 22.

Furthermore, a cam ring 34 as an operation portion side member, that is, an outer cylindrical member is internally fitted into the connection ring 28 substantially coaxially, and this cam ring 34 is not rotatable in a direction around a central axis thereof with respect to the connection ring 28 but is slidable in an axial direction. Further, a protruding end of the cam pin 32 protruding from the first penetrating groove 33 of the connection ring 28 is inserted and engaged into a cam groove 35 spirally formed in the cam ring 34. When the cam pin 32 is in contact with the releasing side end wall of the first penetrating groove 33, the cam pin 32 is disposed at a releasing side end at a proximal end of the cam groove 35 (see a full line in FIG. 4), and the cam ring 34 is disposed at a distal position. On the other hand, when the cam pin 32 is in contact with the fixing side end wall of the first penetrating groove 33, the cam pin 32 is disposed at a fixing side end at a distal end of the cam groove 35 (see a broken line in FIG. 4), and the cam ring 34 is disposed at a proximal position.

It is to be noted that a lateral side on a distal side of the cam groove 35 is opened to the distal side in the cam ring 34. On the other hand, a female screw is formed in the inner peripheral surface of the connection ring 28 on a proximal side with respect to the cam ring 34, and a spring bearing ring 38 having a male screw formed in its outer peripheral surface is threaded and fixed to the female screw. A spring 40 is disposed in a compressed state between the cam ring 34 and the spring bearing ring 38. The cam ring 34 is urged toward the distal side by this spring 40, such that the cam groove 35 is engaged with the cam ring 34.

Here, the cam ring 34 is formed of a rigid member such as a metal or a resin. The rigid member here means a member in which a change of a repulsive force generated due to a deformation of the member with respect to a change of an amount of the deformation has sufficiently great. Further, a friction convex portion is provided to extend over the whole circumference on an inner peripheral surface on the distal side of the cam ring 34. A proximal annular surface of this friction convex portion is substantially perpendicular to the axial direction, and forms a frictional surface 36 described later.

On the other hand, referring to FIG. 2A, an insertion portion connecter 44 is substantially coaxially coupled to a proximal end of a flexible tube 42 in the proximal end of the insertion portion 12. A proximal side of the insertion portion connecter 44 is internally fitted into the operation portion connecter 24 of the operation portion 20 rotatably in a direction around a central axis of this insertion portion connecter 44. It is to be noted that a washer made of a resin having good sliding properties is interposed between the insertion portion connecter 44 and the operation portion connecter 24. Here, a male screw is formed on an outer peripheral surface on a distal side of the insertion portion connecter 44, and a third coupling ring 45 having a female screw formed in its inner peripheral surface is threaded and fixed to the male screw. A proximal end of the anti-bending portion 21 is externally fitted onto and fixed to an outer peripheral surface on a distal side of the third coupling ring 45. Further, an outer peripheral surface on a proximal side of the third coupling ring 45 is internally fitted into the inner peripheral surface at a distal end of the connection ring 28, and the third coupling ring 45 is rotatable with respect to the connection ring 28 integrally with the insertion portion connecter 44.

It is to be noted that an O-ring for securing watertightness even during the rotation of the third coupling ring 45 is interposed between the outer peripheral surface on the proximal side of the third coupling ring 45 and the inner peripheral surface at the distal end of the connection ring 28.

A screw hole penetrates diametrically at the proximal end of the operation portion connecter 24. An end of a fixing pin 46 is threaded into and fixed to this screw hole, and a head portion of the fixing pin 46 protrudes diametrically outwardly. This head portion of the fixing pin 46 is inserted through a second penetrating groove 47 extending in a circumferential direction in the intermediate portion of the operation portion connecter 24. Further, the head portion of the fixing pin 46 is inserted and fitted into and fixed to a fixing hole of a rotary ring 48 as an insertion portion side member, that is, an inner cylindrical member, which is externally fitted onto the proximal end of the operation portion connecter 24 rotatably in a direction around a central axis thereof. That is, the insertion portion connecter 44 and the rotary ring 48 are linked via the fixing pin 46, and are integrally rotatable in a direction around their central axes with respect to the operation portion connecter 24.

A small diameter portion with a small outside diameter is formed on a distal side of the rotary ring 48, and an elastic member 50 in the form of an O-ring is externally fitted into and adhesively fixed to this small diameter portion. Here, the elastic member 50 means a member in which a change of a repulsive force generated due to a deformation of the member with respect to a change of an amount of the deformation has relatively small. In the present embodiment, the elastic member 50 is formed of silicon rubber, fluoro-rubber or the like.

Figure 2B:
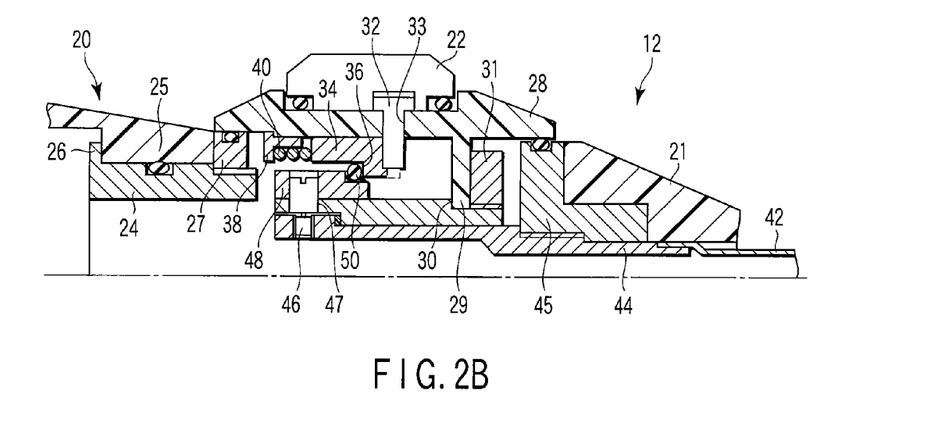
FIG. 2B is a longitudinal sectional view showing the operation force amount adjusting mechanism of the endoscope in a fixed state in the first embodiment of the present invention.

When the cam ring 34 is located at the distal position, the frictional surface 36 of the cam ring 34 and the elastic member 50 of the rotary ring 48 are separated from each other. On the other hand, when the cam ring 34 is located at the proximal position, the elastic member 50 is maximally compressed, and the frictional surface 36 and the elastic member 50 are maximally pressed onto each other. Then, the cam ring 34 is moved in the axial direction in a condition where the frictional surface 36 and the elastic member 50 are pressed onto each other, such that it is possible to continuously adjust the press force acting between the frictional surface 36 and the elastic member 50 while deforming the elastic member 50.

Thus, in the present embodiment, the adjusting ring 22, the cam pin 32 and the cam groove 35 form a movement adjusting mechanism which relatively move the cam ring 34 and the rotary ring 48 to continuously adjust the press force acting between the elastic member 50 and the frictional surface 36 while deforming the elastic member 50.

Furthermore, the insertion portion 12 is rotated with respect to the operation portion 20 in a condition where the frictional surface 36 and the elastic member 50 are pressed onto each other, such that rotation resisting frictional force is generated between the frictional surface 36 and the elastic member 50 in accordance the press force acting between the frictional surface 36 and the elastic member 50.

Next, the function of the endoscope 10 in the present embodiment will be described. When the endoscope 10 is used to observe a body cavity, the insertion portion 12 is operated to rotate with respect to the operation portion 20, and the bending portion 16 is operated to bend in the two directions, thereby orienting the distal rigid portion 14 into a desired direction to insert the insertion portion 12 into the body cavity.

Referring to FIG. 2A, when it is desired to operate to rotate the insertion portion 12 rapidly with respect to the operation portion 20, the adjusting ring 22 is set at the releasing position. As a result, the cam ring 34 is disposed at the distal position, and the frictional surface 36 of the cam ring 34 and the elastic member 50 of the rotary ring 48 are separated from each other. When the insertion portion 12 is operated to rotate with respect to the operation portion 20, the rotation resisting frictional force is not generated between the frictional surface 36 and the elastic member 50, and the operation force amount necessary for the rotational operation becomes sufficiently small.

When it is desired to operate to rotate the insertion portion 12 delicately with respect to the operation portion 20, the adjusting ring 22 is rotationally operated in an amount from the releasing position to the fixing position side. As a result, the cam ring 34 is moved in an amount from the distal position to the proximal side, and the frictional surface 36 and the elastic member 50 are pressed onto each other, thereby the elastic member 50 deforms to compress. When the insertion portion 12 is operated to rotate with respect to the operation portion 20, the rotation resisting frictional force is generated between the frictional surface 36 and the elastic member 50 in accordance the press force acting between the frictional surface 36 and the elastic member 50, so that an operation force amount is necessary for the rotational operation.

Here, when it is desired to slightly decrease the operation force amount necessary for the rotational operation, the adjusting ring 22 is rotationally operated slightly to the releasing position side. As a result, the cam ring 34 is slightly moved to the distal side, and the elastic member 50 slightly deforms to expand, such that the press force acting between the frictional surface 36 and the elastic member 50 is slightly reduced. Here, since the change of the repulsive force due to the change of the deformation amount is relatively small in the elastic member 50, the press force acting between the frictional surface 36 and the elastic member 50 is subtly changed. Then, when the insertion portion 12 is operated to rotate with respect to the operation portion 20, the rotation resisting frictional force generated between the frictional surface 36 and the elastic member 50 is slightly reduced, so that the operation force amount necessary for the rotational operation is slightly reduced.

On the contrary, when it is desired to slightly increase the operation force amount necessary for the rotational operation, the adjusting ring 22 is rotationally operated slightly to the fixing position side. As a result, the cam ring 34 is slightly moved to the proximal side, and the elastic member 50 is slightly compressed, such that the press force acting between the frictional surface 36 and the elastic member 50 is slightly increased. Then, when the insertion portion 12 is operated to rotate with respect to the operation portion 20, the rotation resisting frictional force generated between the frictional surface 36 and the elastic member 50 is slightly increased, so that the operation force amount necessary for the rotational operation is slightly increased.

Referring to FIG. 2B, when it is desired to fix the insertion portion 12 to the operation portion 20, the adjusting ring 22 is set at the fixing position. As a result, the cam ring 34 is disposed at the proximal position, and the elastic member 50 is maximally compressed, so that the frictional surface 36 and the elastic member 50 are maximally pressed onto each other. In this state, the force necessary to start the rotation of the insertion portion 12 (hereinafter referred to as a fixing force amount) is great, and the insertion portion 12 is substantially fixed to the operation portion 20.

Thus, the endoscope 10 of the present embodiment provides the following effects. In the endoscope 10 of the present embodiment, since the cam ring 34 and the rotary ring 48 are relatively moved to continuously adjust the press force acting between the elastic member 50 and the frictional surface 36 while deforming the elastic member 50, the press force acting between the elastic member 50 and the frictional surface 36 can be finely adjusted. Here, in the rotational operation of the insertion portion 12 with respect to the operation portion 20, the rotation resisting frictional force generated between the elastic member 50 and the frictional surface 36 corresponds to the press force acting between the elastic member 50 and the frictional surface 36, so that the frictional force can be finely adjusted. Therefore, the operation force amount necessary for the rotational operation of the insertion portion 12 can be finely adjusted, thereby improving the operability of the endoscope 10.

Furthermore, in the present embodiment, the cam ring 34 and the rotary ring 48 are contained in an internal space formed by the adjusting ring 22, the connection ring 28, the first and third coupling rings 27 and 45, and the insertion portion connecter 44, and the O-rings for maintaining watertightness are disposed in all clearances which might communicate the internal space with the outside. That is, the internal space is kept watertight from the outside, so that the frictional surface 36 of the cam ring 34 and the elastic member 50 of the rotary ring 48 which generate the rotation resisting frictional force in the rotational operation of the insertion portion 12 with respect to the operation portion 20 are kept watertight. Here, when the frictional surface 36 and the elastic member 50 are not kept watertight, the frictional force between the frictional surface 36 and the elastic member 50 decreases due to adhesion of water, blood or the like, or the frictional surface 36 is fixedly attached to the elastic member 50 due to, for example, drying of the adhered blood or mucus, such that the operation force amount necessary for the rotation cannot be properly set. In the present embodiment, the frictional surface 36 and the elastic member 50 are kept watertight, thereby preventing the above situations.

Figure 5:
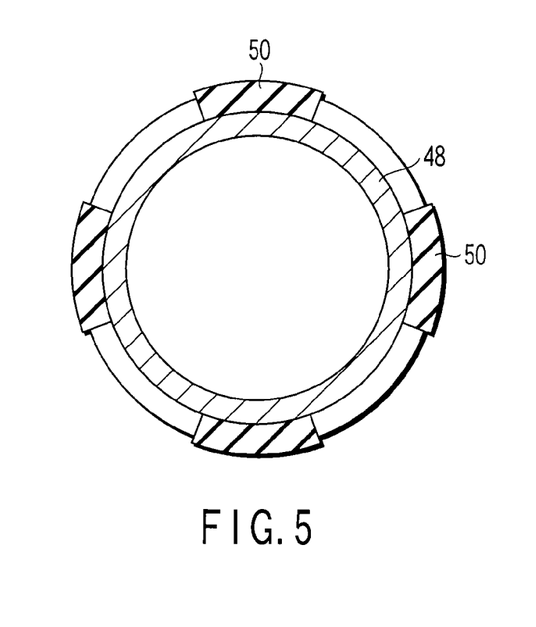
FIG. 5 is a transverse sectional view showing a rotary ring and elastic members of an operation force amount adjusting mechanism of an endoscope in a second embodiment of the present invention.

FIG. 5 shows a second embodiment of the present invention. The same reference numerals are assigned to components having functions similar to those in the first embodiment, and these components are not described. In the rotary ring 48 of the present embodiment, a plurality of elastic members 50 are provided side by side separately from each other in a circumferential direction of the rotary ring 48. Thus, as compared with the first embodiment, the areas of the elastic members 50 pressed onto the frictional surface 36 are reduced, and the press force acting between the frictional surface 36 and the elastic members 50 is increased. Therefore, when the adjusting ring 22 is disposed at the fixing position, the press force acting between the frictional surface 36 and the elastic members 50 is relatively increased, so that the fixing force amount is relatively increased, and the insertion portion 12 can be relatively reliably fixed to the operation portion 20.

Figure 6:
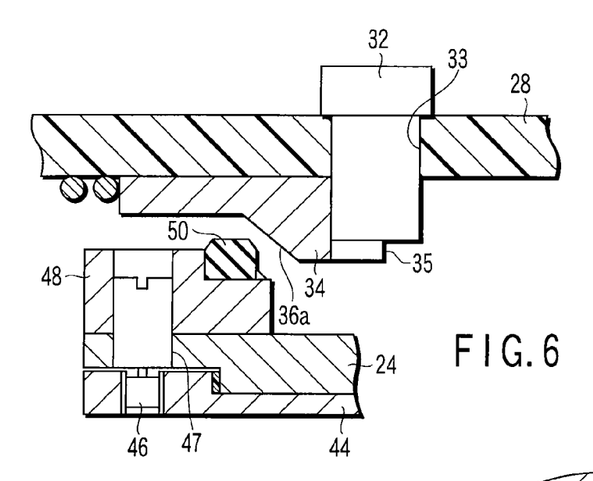
FIG. 6 is a longitudinal sectional view showing an operation force amount adjusting mechanism of the endoscope in a third embodiment of the present invention.

FIG. 6 shows a third embodiment of the present invention. The same reference numerals are assigned to components having functions similar to those in the first embodiment, and these components are not described.

The elastic member 50 of the present embodiment is a trapezoidal ring whose section perpendicular to a circumferential direction is trapezoidal, and the elastic member 50 is formed in the rotary ring 48 by insert molding. Further, the frictional surface 36 of the present embodiment is formed by a tapered surface 36a which comes nearer to the rotary ring 48, that is, decreases in inside diameter from the proximal side to the distal side.

Furthermore, when the adjusting ring 22 is rotationally operated to move the cam ring 34 in the axial direction, the elastic member 50 is gradually deformed while sliding on the tapered surface 36a, so that the press force acting between the tapered surface 36a and the elastic member 50 is adjusted.

Thus, as compared with the first embodiment in which the elastic member 50 is pressed onto the frictional surface 36 substantially perpendicular to the axial direction of the cam ring 34 to adjust the press force, the press force can be more finely adjusted because the elastic member 50 is subtly deformed. Thus, the operation force amount necessary for the rotational operation of the insertion portion 12 can be more finely adjusted, thereby further improving the operability of the endoscope 10.

Figure 7:
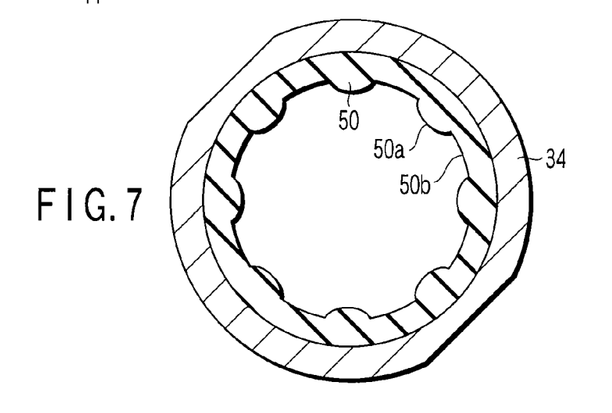
FIG. 7 is a transverse sectional view showing a cam ring and an elastic member of an operation force amount adjusting mechanism of an endoscope in a fourth embodiment of the present invention.
Figure 8A:
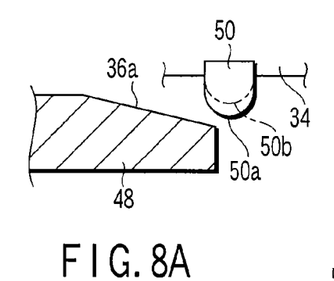
FIG. 8A is a longitudinal sectional view showing the operation force amount adjusting mechanism of the endoscope in a released state in the fourth embodiment of the present invention.
Figure 8B:
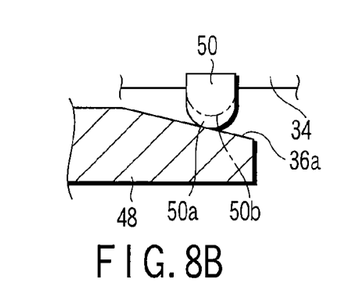
FIG. 8B is a longitudinal sectional view showing the operation force amount adjusting mechanism of the endoscope in an adjusted state in the fourth embodiment of the present invention.
Figure 8C:
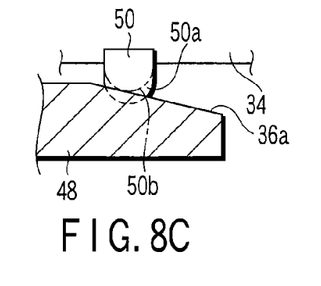
FIG. 8C is a longitudinal sectional view showing the operation force amount adjusting mechanism of the endoscope in a fixed state in the fourth embodiment of the present invention.

FIGS. 7 to 8C show a fourth embodiment of the present invention. The same reference numerals are assigned to components having functions similar to those in the first embodiment, and these components are not described.

Referring to FIGS. 7 and 8A, in the present embodiment, the elastic member 50 is provided to extend over the whole circumference on the inner peripheral surface of the cam ring 34, and convex portions 50a and concave portions 50b are sequentially provided side by side on an inner peripheral surface of the elastic member 50 in the circumferential direction to form an uneven shape. On the other hand, the frictional surface 36 is provided to extend over the whole circumference on an outer peripheral surface of the rotary ring 48, and this frictional surface 36 is formed by the tapered surface 36a which comes nearer to the cam ring 34, that is, increases in outside diameter from the distal side to the proximal side.

Referring to FIG. 8B, when the adjusting ring 22 is rotated to move the cam ring 34 in the axial direction, the convex portions 50a of the elastic member 50 are gradually deformed while sliding on the tapered surface 36a, so that the press force acting between the tapered surface 36a and the convex portions 50a of the elastic member 50 is adjusted. Further, referring to FIG. 8C, when the adjusting ring 22 is set at the fixing position, the cam ring 34 is moved to the proximal position, and the concave portions 50b of the elastic member 50 are pressed onto the tapered surface 36a, and then the uneven shape of the elastic member 50 engages with the tapered surface 36a. It is to be noted that the shape of the elastic member 50 before deformation is indicated by a broken line in FIG. 8C.

Thus, in the present embodiment, the uneven shape of the elastic member 50 engages with the tapered surface 36a when the adjusting ring 22 is set at the fixing position, so that a great fixing force amount is provided, and the insertion portion 12 can be reliably fixed to the operation portion 20.

Figure 9A:
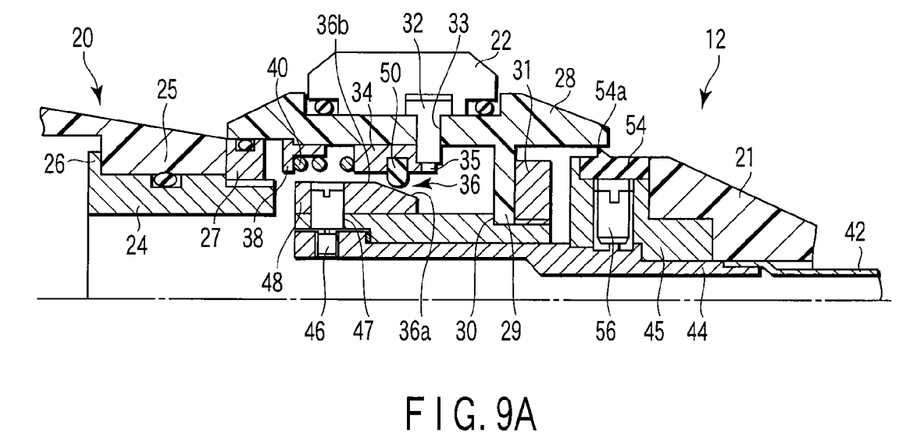
FIG. 9A is a longitudinal sectional view showing an operation force amount adjusting mechanism of an endoscope in a released state in a fifth embodiment of the present invention.
Figure 9B:
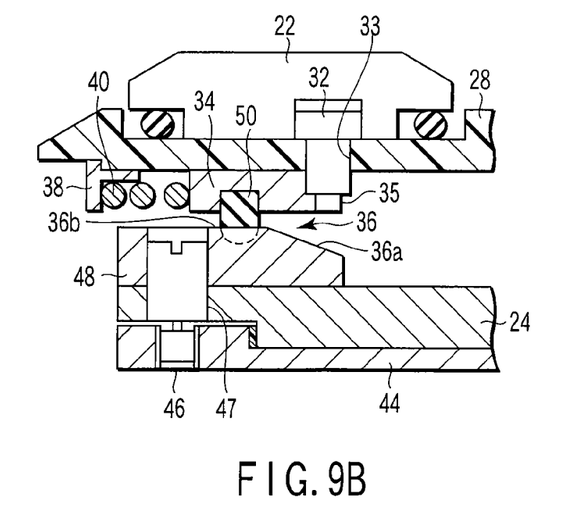
FIG. 9B is a longitudinal sectional view showing the operation force amount adjusting mechanism of the endoscope in a fixed state in the fifth embodiment of the present invention.

FIGS. 9A and 9B show a fifth embodiment of the present invention. The same reference numerals are assigned to components having functions similar to those in the first embodiment, and these components are not described.

Referring to FIG. 9A, in the present embodiment, the elastic member 50 is provided to extend over the whole circumference on the inner peripheral surface of the cam ring 34. That is, a fixing groove is provided to extend over the whole circumference on the inner peripheral surface of the cam ring 34, and a diametrical outer portion of the elastic member 50 is fitted into and fixed to this fixing groove.

On the other hand, the frictional surface 36 is provided to extend over the whole circumference on the outer peripheral surface of the rotary ring 48, and a distal side of this frictional surface 36 is formed by the tapered surface 36a which comes nearer to the cam ring 34, that is, increases in outside diameter from the distal side to the proximal side. Moreover, a proximal side of the frictional surface 36 is formed by a peripheral surface 36b continuously connected to the tapered surface 36a.

It is to be noted that the third coupling ring 45 is not threaded onto the insertion portion connecter 44 in the present embodiment. Instead, a screw hole is formed to diametrically penetrate in the third coupling ring 45, and a fixing screw 56 is screwed into this screw hole to be in contact with the insertion portion connecter 44, thereby fixing the third coupling ring 45 to the insertion portion connecter 44. Moreover, in the outer peripheral portion at the proximal end of the third coupling ring 45, a band member 54 is watertightly provided over the whole circumference in the circumferential direction to cover a diametrical outer opening of the screw hole. In the present embodiment, the band member 54 is formed by a rubber band. A diametrically outwardly protruding portion 54a extends over the whole circumference on an outer peripheral surface of this band member 54. A protruding end of this protruding portion 54a is in contact with the inner peripheral surface at the distal end of the connection ring 28 slidably in the circumferential direction, and secures watertightness between the connection ring 28 and the third coupling ring 45 even during the rotation of the third coupling ring 45.

Next, the function of the endoscope 10 in the present embodiment will be described. When the adjusting ring 22 is rotated to move the cam ring 34 in the axial direction, the elastic member 50 is gradually deformed while sliding on the tapered surface 36a of the frictional surface 36, so that the press force acting between the tapered surface 36a and the elastic member 50 is adjusted. Further, referring to FIG. 9B, when the adjusting ring 22 is set at the fixing position, the cam ring 34 is moved to the proximal position, and the elastic member 50 is disposed on the peripheral surface 36b of the frictional surface 36. As a result, the elastic member 50 is maximally compressed, and maximally pressed and thus held onto the peripheral surface 36b of the frictional surface 36. It is to be noted that the shape of the elastic member 50 before deformation is indicated by a broken line in FIG. 9B.

Furthermore, when the insertion portion 12 is rotated with respect to the operation portion 20, the protruding end of the protruding portion 54a of the third coupling ring 45 slides in contact with the inner peripheral surface at the distal end of the connection ring 28, such that the third coupling ring 45 is watertightly rotated with respect to the connection ring 28.

Thus, the endoscope 10 of the present embodiment provides the following effects. In the present embodiment, when the insertion portion 12 is fixed to the operation portion 20, the elastic member 50 is pressed and held onto the peripheral surface 36b of the frictional surface 36. Therefore, as compared with the case where the elastic member 50 is pressed and held onto the tapered surface 36a of the frictional surface 36, the elastic member 50 can be stably held onto the frictional surface 36, so that a stable fixing force amount is provided, and the insertion portion 12 can be stably fixed to the operation portion 20.

Furthermore, in the present embodiment, when the insertion portion 12 is rotated with respect to the operation portion 20, the protruding end of the protruding portion 54a of the third coupling ring 45 slides in contact with the inner peripheral surface at the distal end of the connection ring 28. Therefore, as compared with the case where the O-ring is interposed between the third coupling ring 45 and the connection ring 28, the third coupling ring 45 can be smoothly rotated with respect to the connection ring 28, and the insertion portion 12 can be smoothly rotated with respect to the operation portion 20.

Figure 10A:
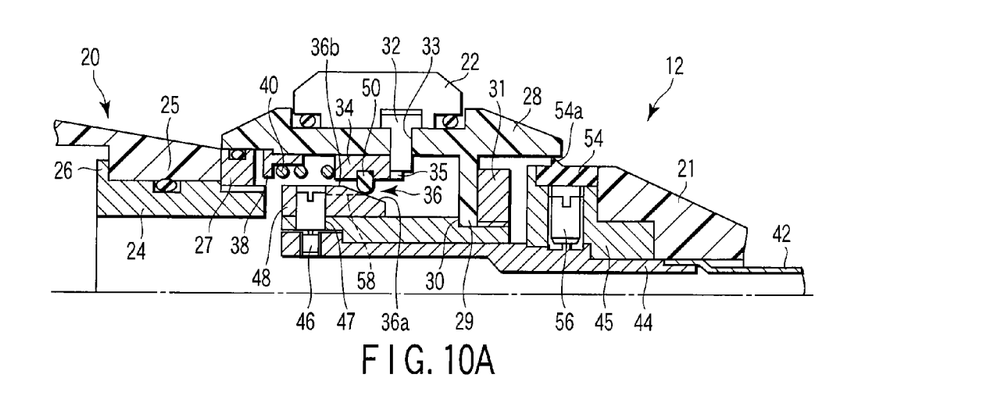
FIG. 10A is a longitudinal sectional view showing an operation force amount adjusting mechanism of an endoscope in a released state in a sixth embodiment of the present invention.
Figure 10B:
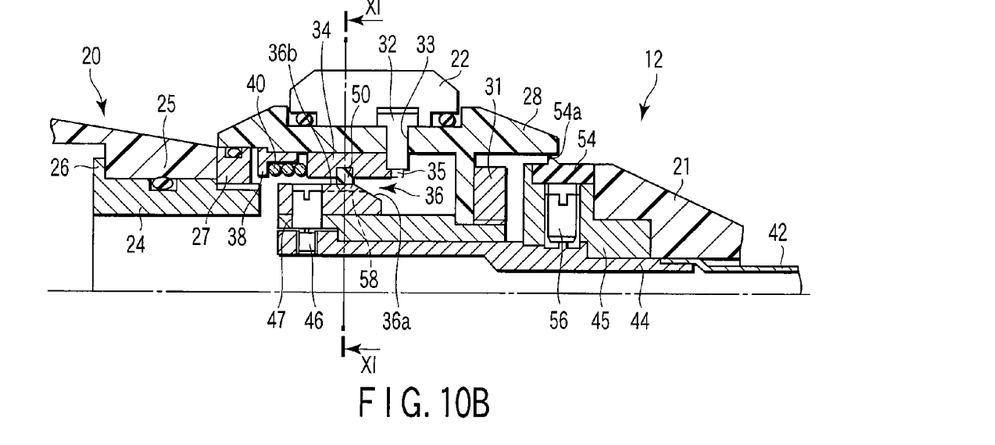
FIG. 10B is a longitudinal sectional view showing the operation force amount adjusting mechanism of the endoscope in a fixed state in the sixth embodiment of the present invention.
Figure 11:
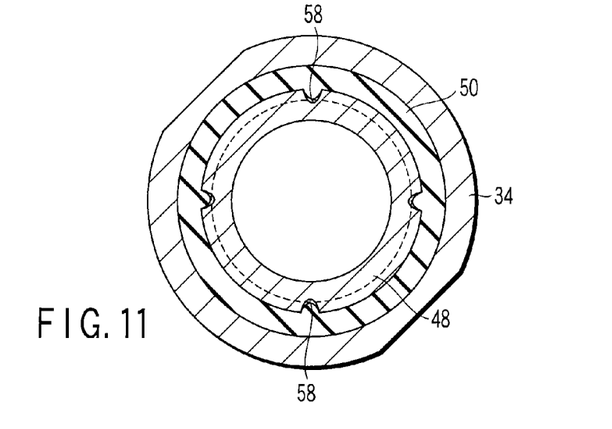
FIG. 11 is a transverse sectional view showing the operation force amount adjusting mechanism of the endoscope in the sixth embodiment of the present invention in the fixed state.

FIGS. 10A to 11 show a sixth embodiment of the present invention. The same reference numerals are assigned to components having functions similar to those in the fifth embodiment, and these components are not described.

Referring to FIG. 10A, in the rotary ring 48 of the present embodiment, a plurality of groove portions 58 are provided to extend in the axial direction all over the peripheral surface 36b from a proximal end of the tapered surface 36a of the frictional surface 36, and the plurality of groove portions 58 are provided side by side in the circumferential direction at an intervals. Thus, an uneven shape is formed on the peripheral surface 36b of the frictional surface 36.

Referring to FIGS. 10B and 11, when the adjusting ring 22 is set at the fixing position, the elastic member 50 is disposed on the peripheral surface 36b of the frictional surface 36, maximally compressed, and maximally pressed and held onto the peripheral surface 36b, and moreover, the elastic member 50 and the uneven shapes of the peripheral surface 36b engage with each other. It is to be noted that the shape of the elastic member 50 before deformed is indicated by a broken line in FIG. 11.

Thus, in the present embodiment, when the insertion portion 12 is fixed to the operation portion 20, the elastic member 50 is pressed and held onto the peripheral surface 36b of the frictional surface 36, and the elastic member 50 engages with the uneven shape of the peripheral surface 36b. Therefore, the elastic member 50 can be stably and reliably engaged with the frictional surface 36, so that a stable and great fixing force amount is provided, and the insertion portion 12 can be stably and reliably fixed to the operation portion 20.

Similar effects can be obtained even if the shapes and the number of uneven shapes are changed.

What is claimed is:

1. An endoscope comprising:
  an operation portion;
  an elongate insertion portion whose one end is connected to the operation portion rotatably in a direction around a central axis of the insertion portion with respect to the operation portion;
  an operation portion side member provided in the operation portion;
  an insertion portion side member provided in the insertion portion and rotatable integrally with the insertion portion;
  an elastic member provided in one of the operation portion side member and the insertion portion side member;
  a frictional surface which is provided in the other of the operation portion side member and the insertion portion side member and which generates rotation resisting frictional force between the frictional surface and the elastic member when the frictional surface is pressed onto the elastic member and the insertion portion is rotated; and
  a movement adjusting mechanism which relatively moves the operation portion side member and the insertion portion side member to continuously adjust press force acting between the elastic member and the frictional surface while deforming the elastic member.

2. The endoscope according to claim 1, wherein
  the operation portion side member and the insertion portion side member are an outer cylindrical member and an inner cylindrical member disposed substantially coaxially with each other;
  the frictional surface is formed in a peripheral surface portion of one of the outer cylindrical member and the inner cylindrical member, the peripheral surface portion being on the side of the other cylindrical member, the frictional surface being substantially perpendicular to an axial direction;
  the elastic member is provided in a peripheral surface portion of the other of the outer cylindrical member and the inner cylindrical member, the peripheral surface portion being on the side of the one cylindrical member; and
  the movement adjusting mechanism relatively moves the outer cylindrical member and the inner cylindrical member in the axial direction, and presses the elastic member onto the frictional surface.

3. The endoscope according to claim 1, wherein
  the operation portion side member and the insertion portion side member are an outer cylindrical member and an inner cylindrical member disposed substantially coaxially with each other;
  the frictional surface is formed in a peripheral surface portion of one of the outer cylindrical member and the inner cylindrical member, the peripheral surface portion being on the side of the other cylindrical member, the frictional surface including a tapered surface which comes nearer to the other cylindrical member from one end side to the other end side of the axial direction;
  the elastic member is provided in a peripheral surface portion of the other of the outer cylindrical member and the inner cylindrical member, the peripheral surface portion being on the side of the one cylindrical member; and
  the movement adjusting mechanism relatively moves the outer cylindrical member and the inner cylindrical member in the axial direction, and slides the elastic member on the tapered surface in the axial direction.

4. The endoscope according to claim 3, wherein
  the frictional surface includes a peripheral surface continuously formed on the other end side of the axial direction from the tapered surface.

5. The endoscope according to claim 3, wherein
  the frictional surface includes an uneven shape which is formed on the other end side of the axial direction of the frictional surface and which engages with the elastic member.

6. The endoscope according to claim 3, wherein
  the elastic member includes an uneven shape which engages with the frictional surface on the other end side of the axial direction of the frictional surface.

* * * * *